US00PP27820P2

(12) United States Plant Patent
Dobres et al.

(10) Patent No.: US PP27,820 P2
(45) Date of Patent: Mar. 28, 2017

(54) ***PENSTEMON* PLANT NAMED 'NOVAPENRUB'**

(50) Latin Name: *Penstemon barbatus*
Varietal Denomination: Novapenrub

(71) Applicant: CP DELAWARE, INC., Wilmington, DE (US)

(72) Inventors: Michael S. Dobres, San Javier (ES); Sloane M. Scheiber, Parkesburg, PA (US)

( * ) Notice: Subject to any disclaimer, the term of this patent is extended or adjusted under 35 U.S.C. 154(b) by 0 days.

(21) Appl. No.: 14/756,948

(22) Filed: Nov. 2, 2015

(51) Int. Cl.
*A01H 5/02* (2006.01)

(52) U.S. Cl.
USPC ..... Plt./465

(58) Field of Classification Search
USPC ..... Plt./465
See application file for complete search history.

*Primary Examiner* — Annette Para
(74) *Attorney, Agent, or Firm* — Buchanan Ingersoll & Rooney PC

(57) ABSTRACT

The new *Penstemon* plant was created by the crossing of parent plants which had been studied in the hope that they might provide desired characteristics. Attractive dark pink blossoms with a white throat are formed in the absence of a vernalization requirement for flowering. An upright compact mounding growth habit is displayed. The plant is well suited for providing attractive ornamentation.

2 Drawing Sheets

Botanical/commercial classification: *Penstemon barbatus/Penstemon* Plant.

Varietal denomination: cv. Novapenrub.

SUMMARY OF THE INVENTION

*Penstemon* plants, sometimes known as Beard Tongue, are herbaceous perennials which provide colorful flowers during the summer.

The new *Penstemon* plant of the present invention was created at West Grove, Pa., U.S.A. A female parent (i.e., seed parent) was selected from a seed mix *Penstemon barbatus* 'Rondo' (non-patented in the United States) on the basis of branching habit, dark purple flower color, and repeat blooming nature. Next, a male parent (i.e. pollen parent) was selected from a seed mix of *Penstemon barbatus* 'Navigator' (non-patented in the United States) on the basis of branching habit, pink flower color, and repeat blooming nature. Seeds from this cross were sown to produce a wide array of plants. What appeared to be promising selections next were made from among the resulting plants. These selections next were assembled and were open pollinated in a controlled environment in a nursery setting.

The plants resulting from the sowing of seeds of this open pollination were physically and biologically different from each other. Selective study resulted in a single plant of the new cultivar and a single plant of the 'Novapenblu' cultivar (U.S. Plant patent application Ser. No. 14/756,947, filed Nov. 2, 2015).

The parentage of the new cultivar can be summarized as follows:

['Rondo'×'Navigator']×Open Pollination.

It was found that the new *Penstemon* plant displays the following combination of characteristics:

(a) displays an upright compact growth habit with strong basal branching, (b) is lacking a vernalization requirement for flowering, (c) forms attractive dark pink blossoms with a white throat, and (d) is well suited for providing attractive ornamentation.

During observations to date, the plant has been found to be hardy in U.S.D.A. Hardiness Zone Nos. 6 to 9. Trimming of the plant promotes further flowering.

The new cultivar well meets the needs of the horticultural industry and can be grown to advantage as a perennial garden plant to provide colorful ornamentation. The plant performs well when grown along borders or sidewalks as well as in containers.

Plants of the new cultivar can be readily distinguished from other *Penstemon* cultivars including its parents. More specifically, 'Rondo' exhibits a considerably taller growth habit, and 'Navigator' commonly displays a wide mix of colored blossoms.

When compared to the 'Hot Pink Riding Hood' cultivar (U.S. Plant Pat. No. 23,089), the new cultivar displays considerably more basal branching. Also, when compared to the 'Novapenblu' cultivar (U.S. Plant patent application Ser. No. 14/756,947, filed Nov. 2, 2015), the 'Novapenpin' cultivar (U.S. Plant Pat. No. 26,701) and the 'Novapenpur' cultivar (U.S. Plant patent application Ser. No. 13/998,817, filed Dec. 11, 2013, it is found that the 'Novapenblu' cultivar displays bluish-purple blossoms, the 'Novapenpin' cultivar displays lighter colored blossoms, and the 'Novapenpur' cultivar displays dissimilar dark purple blossoms.

The rooting of vegetative cuttings has been used to asexually propagate the new cultivar at West Grove, Pa., U.S.A. It has been found that the characteristics of the new cultivar are stable and are reliably transmitted from one generation to another. Accordingly, the new cultivar can be asexually reproduced in a true-to-type manner.

The new cultivar of the present invention has been named 'Novapenrub', and will be marketed under the RUBY ROCK CANDY Trademark.

BRIEF DESCRIPTION OF THE PHOTOGRAPHS

The accompanying photographs illustrate typical flowering plants of the new cultivar in color as nearly true as it is reasonably possible make the same in color illustrations of this nature. The plants were approximately one year of age and were being grown outdoors in containers in full sun during August 2014 at West Grove, Pa., U.S.A. The plants had been asexually reproduced by the rooting of vegetative cuttings.

DETAILED BOTANICAL DESCRIPTION

Figure 1:
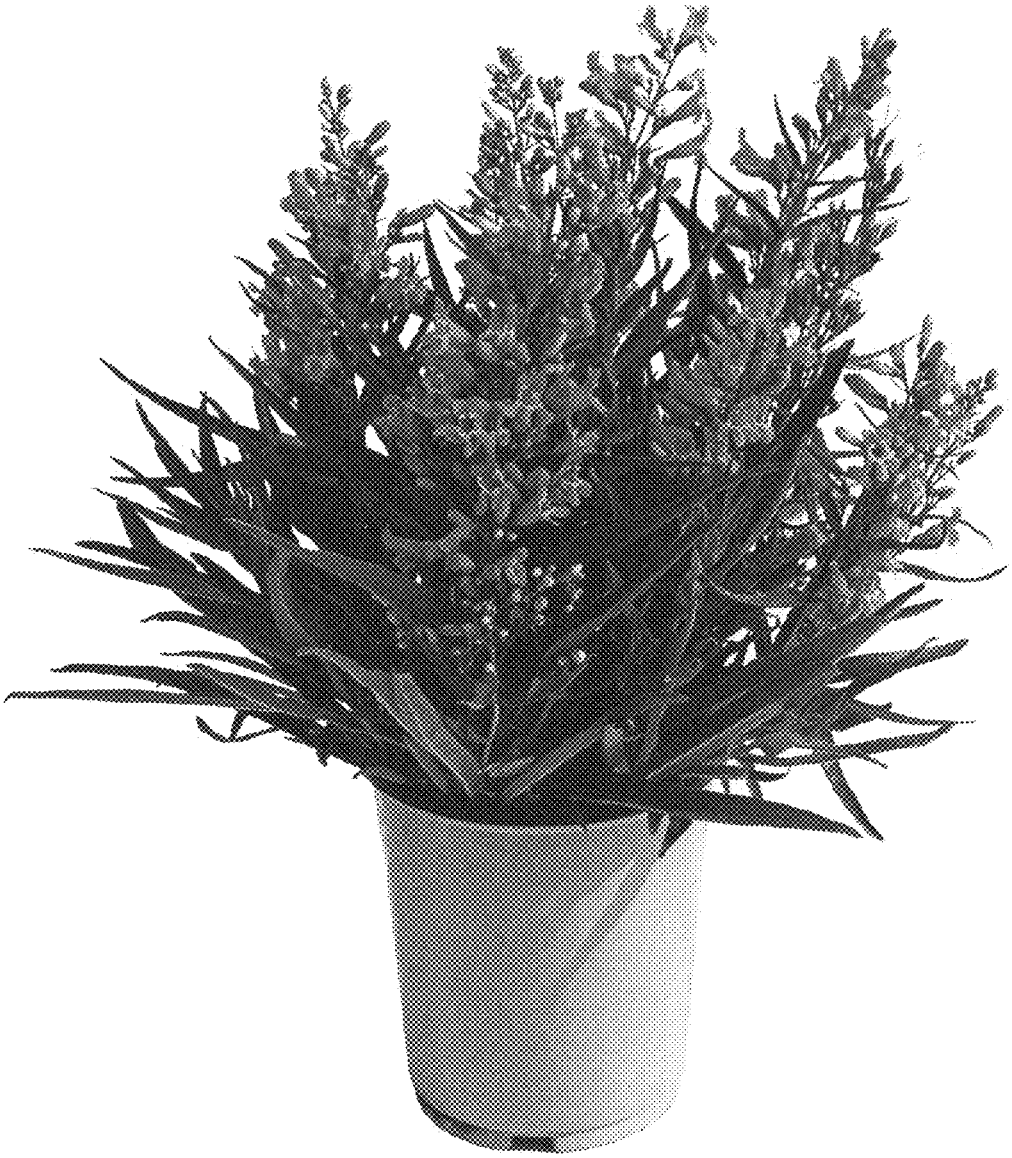
FIG. 1 illustrates the upright compact growth habit of a flowering plant of the new cultivar.
Figure 2:
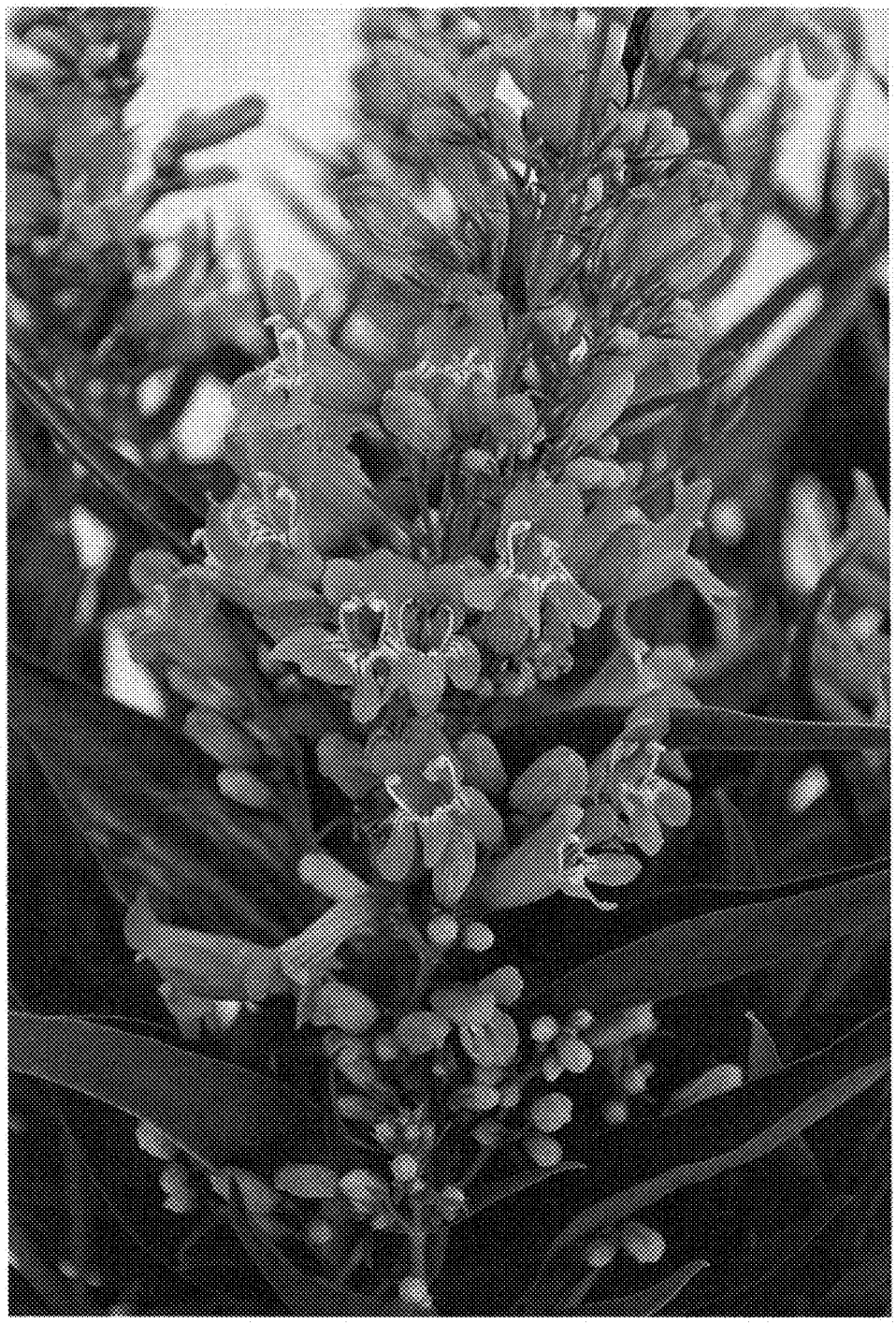
FIG. 2 illustrates a close view of the blossoms in various stages of development and the foliage of the new cultivar.

The following is a detailed description while observing one-year-old plants of the new cultivar that were produced by the rooting of vegetative cuttings. Such plants were being grown during June 2015 in one-gallon containers outdoors at West Grove, Pa., U.S.A. The chart used in the identification of color is The R.H.S. Colour Chart (1995 Edition) of The Royal Horticultural Society, London, England. Common color terms are to be accorded their customary dictionary significance.

Botanical classification: *Penstemon barbatus*, cv. Novapenrub.

*Parents*.—Cross of seed mixtures of *Penstemon barbatus* 'Rondo' and 'Navigator' with some selection followed by open pollination to produce progeny and an ultimate selection from within such progeny.

*Plant type*.—Herbaceous perennial.

Plant:

*Growth habit*.—Upright and compact.

*Height*.—Approximately 30 to 45 cm on average when mature. During observations, the 'Rondo' ancestor has assumed a height of approximately 60 cm.

*Spread*.—Approximately 30 to 45 cm on average when mature.

*Branching*.—Commonly approximately 9 lateral stems arise at the base. During observations at West Grove, Pa., U.S.A., this compares to approximately 2 or 3 basal branches for the 'Hot Pink Riding Hood' cultivar.

*Branch length*.—Commonly approximately 23 cm on average.

*Branch diameter*.—Commonly approximately 4 mm on average.

*Stem strength*.—Relatively strong.

*Stem color*.—Near Green Group 143C.

*Stem texture*.—Smooth.

*Internode length*.—Commonly approximately 3.5 cm.

*Roots*.—Fibrous network.

Foliage:

*Arrangement*.—Opposite, simple, sessile.

*Shape*.—Broadly lanceolate.

*Apex*.—Acuminate.

*Base*.—Truncate.

*Length*.—Commonly approximately 12 to 18 cm on average.

*Width*.—Commonly approximately 1.5 to 2.5 cm on average.

*Texture*.—Smooth on the upper and under surfaces.

*Color*.—On the upper surface near Green Group 137C, and on the lower surface near Green Group 138B.

*Margins*.—Entire.

Inflorescence:

*Season*.—The natural flowering season when grown outside primarily is May to July.

*Type*.—Single bi-labiate, arranged on terminal racemes, and with flowers mostly facing outwards.

*Buds*.—Ovoid, approximately 2 cm in length on average just before opening, approximately 6 mm in diameter, and near Red-Purple Group 70C in coloration.

*Quantity*.—Free-flowering, commonly with approximately 50 flowers on average developing per inflorescence.

*Flower diameter*.—Approximately 8 mm on average.

*Flower length*.—Approximately 3 cm on average.

*Petal number*.—Five.

*Petal arrangement*.—Petals fused into a tube, bi-labiate, upper lip with two upper petals, and lower lip with three lower petals.

*Petal length*.—Approximately 4 to 6 mm on average.

*Petal width*.—Approximately 3 to 5 mm on average.

*Petal shape*.—Substantially round.

*Petal apex*.—Rounded.

*Petal margin*.—Entire.

*Petal texture*.—Smooth on upper and under surfaces.

*Petal color*.—Upper surface: when opening near Red-Purple Group 67B, and when fully open near Red-Purple Group 67A. Lower surface: when opening near Red-Purple Group 70C, and when fully open near Red-Purple Group 70A.

*Throat color*.—The tube commonly is near White Group 155A.

*Sepal arrangement*.—In a single whorl, and with a salverform calyx.

*Sepal shape*.—Lanceolate.

*Sepal apex*.—Pointed.

*Sepal base*.—Truncate.

*Sepal margin*.—Entire.

*Sepal texture*.—Smooth on upper and under surfaces.

*Sepal color*.—Near Yellow-Green Group 144A on both surfaces.

*Sepal number*.—Five.

*Anther opening*.—Tend to dehisce the full length across the connective and usually spread widely apart.

*Anther length*.—Approximately 3 mm on average.

*Anther color*.—Near Yellow-Orange Group 19D.

*Filaments*.—Commonly approximately 2 cm in length on average, and near White Group 155C in coloration.

*Pollen*.—Present in a moderate quantity, and near Yellow-Orange Group 19D in coloration.

*Staminoid*.—One, approximately 2 cm in length, approximately 0.5 mm in diameter, and near White Group 155C in coloration.

*Pistil number*.—One.

*Pistil length*.—Approximately 2 cm on average.

*Style length*.—Approximately 1.5 cm on average.

*Style color*.—White Group 155C with near Yellow-Green Group 145A at the base and apex.

*Stigma color*.—Near White Group 155C.

*Stigma shape*.—Flattened.

*Ovary color*.—Near Yellow-Green Group 145B.

*Seeds/fruit*.—Have not been observed.

*Fragrance*.—None detected.

*Peduncle length*.—Approximately 1.5 cm on average.

*Peduncle diameter*.—Approximately 1.5 mm on average.

*Peduncle aspect*.—Commonly up straight.

*Peduncle texture*.—Smooth.

*Peduncle strength*.—Relatively strong.

*Peduncle color*.—Near Green Group 143C.

*Pedicel length*.—Approximately 5 mm on average.

*Pedicel diameter*.—Approximately 1 mm on average.

*Pedicel aspect*.—Commonly up straight.

*Pedicel strength*.—Moderately strong.

*Pedicel color*.—Near Green Group 143C.

Disease resistance: The tolerance/susceptibility to diseases and pests common to *Penstemon* plants appears to be typical during observations to date.

Plants of the 'Novapenrub' cultivar have not been observed under all possible environmental conditions to date. Accordingly, it is possible that the phenotypic expression may vary somewhat with changes in light intensity and duration, cultural practices, and other environmental conditions.

We claim:

1. A new and distinct *Penstemon* plant having the following combination of characteristics:

(a) displays an upright compact growth habit with strong basal branching, (b) is lacking a vernalization requirement for flowering, (c) forms attractive dark pink blossoms with a white throat, and (d) is well suited for providing attractive ornamentation; substantially as illustrated and described.

* * * * *